United States Patent
Chopdekar et al.

(10) Patent No.: US 7,388,001 B1
(45) Date of Patent: *Jun. 17, 2008

(54) HALIDE-FREE GLUCOSAMINE SULFATE COMPOSITIONS AND METHODS OF PREPARATION

(75) Inventors: Vilas M. Chopdekar, Edison, NJ (US); Michelle Y. McGough, Lebanon, IN (US); Hemant S. Desai, Piscataway, NJ (US); James G. Schleck, Metuchen, NJ (US); Sham N. Redkar, Bound Brook, NJ (US)

(73) Assignee: JFC Technolries, LLC, Bound Brook, NJ (US)

( * ) Notice: Subject to any disclaimer, the term of this patent is extended or adjusted under 35 U.S.C. 154(b) by 103 days.

This patent is subject to a terminal disclaimer.

(21) Appl. No.: 11/223,687

(22) Filed: Sep. 9, 2005

Related U.S. Application Data

(60) Provisional application No. 60/611,182, filed on Sep. 17, 2004.

(51) Int. Cl.
*A61K 31/70* (2006.01)
*C07H 5/04* (2006.01)

(52) U.S. Cl. ............... 514/62; 536/55.2; 536/55.3
(58) Field of Classification Search .......... 536/55.2, 536/55.3; 514/63
See application file for complete search history.

(56) References Cited

U.S. PATENT DOCUMENTS

| | | | |
|---|---|---|---|
| 3,683,076 A | 8/1972 | Rovati | 424/180 |
| 4,499,078 A | 2/1985 | Revici | 424/153 |
| 4,642,340 A | 2/1987 | Senin et al. | 536/55.2 |
| 5,843,923 A | 12/1998 | Schleck et al. | 514/62 |
| 5,902,801 A | 5/1999 | Schleck et al. | 514/62 |
| 6,346,519 B1 * | 2/2002 | Petrus | 514/62 |
| 6,472,380 B1 | 10/2002 | Schleck et al. | 514/62 |
| 6,486,307 B1 | 11/2002 | Gandhi et al. | 536/20 |
| 2003/0148998 A1 | 8/2003 | Fan et al. | |
| 2004/0030121 A1 | 2/2004 | Mukhopadhyay et al. | 536/55.2 |
| 2004/0077055 A1 | 4/2004 | Fosdick et al. | 435/85 |
| 2004/0091976 A1 | 5/2004 | Deng et al. | 435/84 |
| 2005/0014720 A1 | 1/2005 | Vila Pahi et al. | 514/62 |
| 2005/0148546 A1 | 7/2005 | Grund et al. | 514/62 |

FOREIGN PATENT DOCUMENTS

| | | |
|---|---|---|
| EP | 0 214 642 A2 | 3/1987 |
| GB | 1056331 | 1/1967 |

OTHER PUBLICATIONS

Murray, Michael t., N.D., *Vital Communications, Inc.*, Jul. 1998.
Medsafe Data Sheet: Sodium chloride injection BP 0.9%.
QJM: "Adverse Reactions to Potassium Chloride".
"Potassium Chloride (KCl) Slow Release (SR)".

* cited by examiner

*Primary Examiner*—Elli Peselev
(74) *Attorney, Agent, or Firm*—Jack Matalon

(57) ABSTRACT

Glucosamine sulfate having a purity of at least about 99 wt. %, and a maximum halide content of about 0.01 wt. %. Preferably, the glucosamine sulfate is stabilized by coating it with at least one pharmaceutically acceptable polymer comprising a water-soluble, water-immiscible and/or water-swellable homopolymer and/or copolymer. Suitable polymers include carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers. The resultant coated glucosamine sulfate composition will be stable at ambient temperatures and upon exposure to the atmosphere.

18 Claims, No Drawings

HALIDE-FREE GLUCOSAMINE SULFATE COMPOSITIONS AND METHODS OF PREPARATION

CROSS-REFERENCE TO RELATED APPLICATION

This application claims the benefit of Provisional Application Ser. No. 60/611,182 filed Sep. 17, 2004.

FIELD OF THE INVENTION

The invention relates to halide-free glucosamine sulfate, stabilized halide-free glucosamine compositions and methods for preparing such glucosamine sulfate and stabilized glucosamine sulfate compositions.

BACKGROUND OF THE INVENTION

Glucosamine is a well-known amino monosaccharide found in chitin, glycoproteins and glycosaminoglycans. Glucosamine is widely used for the treatment of rheumatic fever, arthritic and arthosic complaints, in the acute as well as chronic forms, as well as in the treatment of pathological conditions originating from metabolic disorders of the osteoarticular tissue. Although products in the marketplace are labeled as, or referred to as, "glucosamine" or "stabilized glucosamine", they are misnomers, since such products consist of glucosamine hydrochloride or unreacted mixtures of glucosamine hydrochloride and a salt such as potassium or sodium sulfate.

Mixed salts of glucosamine hydrochloride and alkaline or earth alkaline metal sulfates such as potassium sulfate, and sodium sulfate are well known. Such mixed salts are used rather than glucosamine sulfate alone since the latter is unstable in view of its highly hygroscopic nature and the facility with which its amino group oxidizes if not completely saltified, see, e.g., U.S. Pat. No. 4,642,340 and U.S. Pat. No. 3,683,076 which disclose mixtures of glucosamine sulfate and glucosamine hydroiodide.

Free glucosamine base may be prepared by the method recited in *Chem. Ber.*, volume 75, page 1274. Such method involved the treatment of glucosamine hydrochloride with an ethanolic solution of a tertiary base such as triethylamine. Triethylamine hydrochloride is filtered off and the free glucosamine is then recovered from the reaction mixture. However, triethylamine is a toxic material even in small quantities and the yield of the free glucosamine base is quite low. Moreover, the free glucosamine base still contains residual chloride.

In EP 0 214 642, free glucosamine base containing residual chloride is converted to a mixed salt of glucosamine sulfate and potassium chloride by dissolving the glucosamine base in water, adding a stoichiometric quantity of concentrated sulfuric acid to form a solution of glucosamine sulfate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0° C. and recovering the precipitated salt by filtration. This process results in low yields.

Free glucosamine base may also be prepared by microbial fermentation. For example, see US Published patent application Publication Nos. 2004/0091976 A1, 2004/0077055 A1 and 2003/0148998 A1. It is known to prepare glucosamine by deacetylation of n-acetyl-glucosamine, see US Published patent application Publication No. 2005/0145846 A1. Glucosamine hydrochloride may also be prepared by the process disclosed in U.S. Pat. No. 6,486,307; the process involves the grinding of chitin to a very fine size, followed by digestion with concentrated hydrochloric acid. The crude glucosamine hydrochloride is then decolorized with activated charcoal and assayed by pH titration with a base.

In US Published patent application 2004/0030121, free glucosamine base containing residual chloride is converted to a mixed salt of glucosamine sulfate and potassium chloride by dissolving the glucosamine base in water, adding a stoichiometric quantity of concentrated sulfuric acid to form a solution of glucosamine sulfate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0° C. and recovering the precipitated salt by filtration. This process results in low yields.

Regardless of the source of the glucosamine, it is commercially available only in the form of a halide salt, usually the hydrochloride, since the glucosamine free base can only be isolated from aqueous reaction mixtures in the form of its salt. Furthermore, free glucosamine base is unstable at ambient temperatures and is quite hygroscopic and it is therefore converted to a halide salt before being marketed.

In co-pending patent application Ser. No. 11/223,236 filed Sep. 9, 2005 (corresponding to provisional application No. 611,709 filed Sep. 17, 2004), the disclosure of which is incorporated herein in its entirety by reference, a process is disclosed for converting a glucosamine halide into a halide-free glucosamine base. The resultant halide-free glucosamine base may then be used as is for those medicinal purposes in which the presence of a salt such as sodium or potassium chloride, sodium or potassium sulfate, sodium or potassium iodide, etc. is undesirable. The halide-free glucosamine base may also be employed to prepare a wide variety of useful derivatives such as glucosamine salts, e.g., glucosamine sulfate, glucosamine phosphate, glucosamine salts of α-hydroxy acids (e.g., lactic acid, citric acid, etc.), n-acetylglucosamine, glucosamine salts of drugs having acidic functionalities, etc., wherein such derivatives do not contain any objectionable cations such as sodium or potassium.

The halide-free glucosamine base prepared by the process disclosed in the above-identified co-pending application may be readily converted into halide-free glucosamine sulfate by the method described below. However, the resultant halide-free glucosamine sulfate is unstable—it is quite hygroscopic and will readily decompose when exposed to ambient temperatures and/or the atmosphere. Therefore, the halide-free glucosamine sulfate composition must be kept refrigerated in a closed container, thereby limiting the usefulness of the composition. It would be most desirable if a method could be found for stabilizing the glucosamine sulfate without having any adverse effect on the physical and chemical properties of the glucosamine sulfate such that the glucosamine sulfate could be exposed to the atmosphere and stored at ambient temperatures without decomposition occurring.

DETAILS OF THE INVENTION

The invention relates to glucosamine sulfate and stabilized glucosamine sulfate compositions and methods for preparing such glucosamine sulfate and stabilized glucosamine sulfate compositions. Not only is the glucosamine sulfate of the invention free of halide, but is also free of the salts that are present in currently available "glucosamine sulfate" compositions such as those described in U.S. Pat. Nos. 5,843,923, 5,902,801 and 6,472,380. Thus a patient who cannot or who does not wish to ingest salts when ingesting currently available "glucosamine sulfate" may now be able to ingest true glucosamine sulfate containing neither extraneous cations nor anions.

The starting material for preparing the glucosamine sulfate of the invention comprises a halide-free glucosamine base, which may be prepared by the method disclosed in the above-identified co-pending patent application. Such method involves the following steps:

(a) a glucosamine halide salt (e.g., glucosamine hydrochloride, glucosamine hydroiodide, etc.) is reacted with a lithium base in the presence of a $C_1$-$C_4$ alcohol to thereby generate a $C_1$-$C_4$ alcohol solution of a lithium halide and an insoluble halide-free glucosamine base; and (b) the insoluble halide-free glucosamine base is separated from the $C_1$-$C_4$ alcohol solution of the lithium halide salt.

For maximum yields, the reaction should be carried out at a temperature of about 15 to about 35° C.; conveniently, the reaction may be carried out at ambient temperatures.

The $C_1$-$C_4$ alcohol may be, e.g., methanol, ethanol (preferably anhydrous), isopropanol, etc.; the preferred alcohol comprises methanol. The lithium base may be anhydrous lithium hydroxide, lithium hydroxide monohydrate, lithium methoxide, lithium ethoxide or lithium isopropoxide. The preferred lithium base comprises anhydrous lithium hydroxide. It has been found that the presence of water in the reaction mixture reduces the yield of the halide-free glucosamine base. Accordingly, it is preferred that the reaction be carried out under anhydrous conditions. In general, the lithium base is employed in an amount of about 1.0 to about 1.2 moles per mole of halide present in the glucosamine halide salt. Excess lithium base is unnecessarily wasteful and will reduce the yield of the halide-free glucosamine base. Typically, the alcohol is employed in an amount of about 1 to about 10 parts, preferably 3 to 6 parts, per part of lithium base.

After allowing the reaction to proceed (preferably with agitation) for about 5 minutes to about 2 hours, the solid halide-free glucosamine base is filtered off from the resultant alcohol solution of the lithium halide and washed with additional alcohol. The halide-free glucosamine base may then be dried under vacuum at a temperature of about 15 to about 30° C. The yield typically ranges from about 85 to about 90%. The halide-free glucosamine base is quite pure. It will have a purity level of at least about 99 wt. % and the halide content will be a maximum of about 0.01 wt. %, e.g., 100 ppm or less and very often, the halide content will be less than 50 ppm. Based upon the residual halide content of the halide-free glucosamine base, the lithium residue in the glucosamine base will generally be a maximum 20 ppm and often, the lithium residue content will be less than 10 ppm.

The halide-free glucosamine base is quite hygroscopic and will decompose over a period of time if exposed to ambient temperature and/or to the atmosphere. Accordingly, it should be refrigerated in a closed container or preferably promptly used after recovery for conversion to the glucosamine sulfate of the invention as described below.

The halide-free glucosamine base may be readily converted to the glucosamine sulfate of the invention by reacting it with a stoichiometric amount of aqueous sulfuric acid. Typically, the reaction mixture will comprise the glucosamine base, about 5 to about 30 parts, preferably 15 to 20 parts, of water (preferably purified water) per part of the base and aqueous sulfuric acid in a concentration of about 80 to about 100%. Although lesser amounts of water may be employed, the resultant solutions may become too viscous to be properly agitated, particularly if the halide-free glucosamine sulfate is not isolated from the reaction mixture, but is stabilized by the addition of a polymer to the reaction mixture, as described below. On the other hand, excessive amounts of water may lead to reduced yields if a water-miscible solvent is used to recover the composition and if freeze-drying is used to recover the composition, the freeze-drying process becomes more time-consuming and expensive because of the large amount of water to be removed from the reaction mixture.

The sulfuric acid is generally present in a stoichiometric amount based on the number of moles of the glucosamine base present in the reaction mixture (one mole of sulfuric acid will be required per two moles of the base). The aqueous sulfuric acid is slowly added to the aqueous solution of the glucosamine base while aqueous solution is agitated, e.g. over a period of a few minutes, and the reaction mixture is further agitated for 5 to 120 minutes. The reaction is exothermic in nature and therefore the temperature is typically controlled to remain within the range of about 0 to about 15° C.

Thereafter, the glucosamine sulfate of the invention may be recovered from the reaction mixture by freeze-drying or by adding a water-miscible solvent such as acetone to the reaction mixture such that the glucosamine sulfate will precipitate from the reaction mixture and the product is then recovered by conventional filtration methods. The halide-free glucosamine sulfate may then be dried by conventional methods, e.g., a stream of nitrogen, a vacuum oven at 30-50° C. for a period of 1 to 10 hours, etc. It is preferred that the recovery of the glucosamine sulfate composition of the invention be carried out by a freeze-drying process as described in greater detail below.

The glucosamine sulfate of the invention is quite hygroscopic and it will decompose over a period of time if it is exposed to ambient temperatures or the atmosphere. Therefore, it is preferred that the glucosamine sulfate not be isolated from the reaction mixture as is, but converted to a stabilized form prior to recovery from the reaction mixture.

Stabilization of the glucosamine sulfate of the invention is readily accomplished by adding a suitable pharmaceutically acceptable polymer to the reaction mixture prior to recovery of the composition. The pharmaceutically acceptable polymer may be a water-soluble, water-dispersible and/or or a water-swellable homopolymer and/or copolymer. Preferably, the pharmaceutically acceptable polymer will be water-soluble. In general, the polymer will be employed in an amount of about 2 to about 70, preferably 20 to 50, parts by weight of the polymer per part of the glucosamine sulfate. Nonlimiting examples of commercially available pharmaceutically acceptable homopolymers and copolymers suitable for stabilizing the glucosamine sulfate include the following: carboxypolymethylene homopolymers and copolymers, i.e., vinyl polymers having active carboxyl groups such as high molecular weight homopolymers of acrylic acid crosslinked with allylsucrose or allylpentaerythritol and copolymers of acrylic acid modified by long chain ($C_{10}$-$C_{30}$) alkyl acrylates and crosslinked with allylpentaerythritol—such polymers are commercially available and are marketed as Carbopol® polymers; polyethylene glycol homopolymers and copolymers (e.g., polyethylene-co-lactic acid copolymers), particularly polyethylene glycol polymers having molecular weights in the range of about 2,000 to about 20,000, preferably 4,000 to 18,000; polypropylene glycol homopolymers and copolymers, especially polypropylene glycol homopolymers having molecular weights of about 800 to about 18,000; ethylcellulose; povidone homopolymers, i.e., synthetic water-soluble homopolymers of N-vinyl-pyrrolidone, especially those having a molecular weight of about 2,500 to about 10,000; copovidone, i.e. synthetic random copolymers of N-vinylpyrrolidone and vinyl acetate in a 60:40 ratio; polyacrylic acid homopolymers and copolymers; polyacrylamide homopolymers and copolymers; polysaccharides; etc.

The choice of particular homopolymers and/or copolymers for coating, i.e., stabilizing, the glucosamine sulfate is not critical so long as the polymers are pharmaceutically acceptable, have the capability of coating, i.e., stabilizing, the halide-free glucosamine sulfate without any adverse chemical reaction occurring between the selected polymers and the glucosamine sulfate and the resultant coated glucosamine sulfate compositions are stable, i.e., they will not undergo decomposition when exposed to ambient temperatures and/or the atmosphere.

If the glucosamine sulfate is to be recovered from the reaction mixture in a stabilized form, the desired pharmaceutically acceptable polymer is added, preferably in increments, with stirring, to the aqueous solution of the glucosamine base. This step will generally take about 5 to about 15 minutes and is preferably conducted at a temperature of about 15 to about 40° C. After all increments of the selected polymer have been added, stirring is continued for an additional 5 to 120 minutes. Thereafter, aqueous sulfuric acid is slowly added, with stirring, to the reaction mixture, while maintaining the reaction mixture at a temperature of about 0 to about 15° C. (the reaction is exothermic).

The last step is the recovery of the polymer-coated, i.e., stabilized, glucosamine sulfate composition from the reaction mixture. The stabilized halide-free glucosamine sulfate composition is recovered from the reaction mixture by freeze-drying or by adding a water-miscible solvent, e.g., acetone, to the reaction mixture to cause the stabilized halide-free glucosamine sulfate composition to precipitate out from the reaction mixture. The precipitate is then recovered by conventional filtration methods and it may be dried as described below. Of course, the choice of stabilizing polymer and water-miscible solvent should be such that the polymer will not dissolve in, or otherwise react with, the solvent.

The stabilized glucosamine sulfate composition is preferably recovered by removal of water from the reaction mixture by freeze-drying, a well-known technique for removing water from compositions. Although freeze-drying is a time-consuming process, (a reaction mixture containing one liter of water will typically require 30-36 hours to remove about 97% of the water), it is preferred since the formation of decomposition products resulting from heating the reaction mixture or adding solvents to the reaction mixture can be avoided.

The freeze-drying process will generally be carried out at a reduced pressure and reduced temperature, e.g., a pressure of not greater than 500 milliTorre, preferably 300 to 100 milliTorre and at a temperature of about −60 to about −20° C., preferably −50 to −40° C. The endpoint of completion of the freeze-drying process may be determined by condensing and measuring the quantity of water removed during the freeze-drying process. The time required for completion of the freeze-drying process will vary depending on factors such as pressure, temperature, quantity of reaction mixture to be free-dried, level of water to be tolerated in the stabilized halide-free glucosamine sulfate composition, the thickness and surface area of the reaction mixture in the trays of the freeze-drying equipment, etc.

If the stabilized halide-free glucosamine sulfate composition is to be recovered by precipitation from the reaction mixture by addition of a water-miscible solvent such as acetone to the reaction mixture, generally about 2 to about 10 parts of solvent per part of reaction mixture will be required.

After the stabilized glucosamine sulfate composition has been recovered from the reaction mixture, it may be dried by conventional techniques, e.g., a stream of nitrogen, vacuum oven at a temperature of about 30 to about 50° C. for 1 to 10 hours or more, etc.

It should also be noted that the stabilization of the glucosamine sulfate of the invention offers an additional advantage to the patients who ingest such compositions. The stabilized, i.e., polymer-coated, versions of the glucosamine sulfate provide extended release properties, i.e., the glucosamine sulfate is released within the patient over an extended period of time, thereby minimizing gastric intolerance problems and also resulting in a reduction of the dosage that is required to be ingested over a particular time frame.

The following nonlimiting examples shall serve to illustrate the preferred embodiments of the invention. Unless otherwise indicated, all parts and percentages are on a weight basis.

Example 1

In a reaction vessel were added 17.9 g (0.1 mole) of halide-free glucosamine base and 125 cc of purified water. The mixture was stirred until the base had dissolved. Thereafter, 11.5 g of polyethylene glycol homopolymer having a molecular weight of 4,000 were added and the mixture was stirred until a clear solution was obtained. The solution was cooled to a temperature of 5 to 10° C. and 4.9 g of concentrated sulfuric acid were slowly added to the reaction mixture, while stirring and maintaining a temperature of 5 to 10° C. After all of the sulfuric acid was added, the pH was 3.5. The reaction mixture was stirred for an additional 30 minutes and the resultant stabilized glucosamine sulfate product was isolated by freeze-drying at a pressure of about 200 milliTorre and a temperature of about −45° C. The yield of snow-white product was 33 g (96%). The specific optical rotation of the stabilized glucosamine sulfate was found to be 62.99°. The product was stored in a capped bottle at ambient temperature and remained snow-white in color after a period of one year.

Example 2

Example 1 was repeated using 11.5 g of polyethylene glycol homopolymer having a molecular weight of 8,000 rather than the 4,000 molecular weight polymer employed in Example 1. The same yield of snow-white product was obtained. In this case, the stabilized glucosamine sulfate has a specific optical rotation of 63.53°.

Example 3

This example was carried out to determine the purity of the stabilized glucosamine sulfate prepared in example 1, i.e., to determine whether a true sulfate salt of the glucosamine base had been prepared. In a reaction vessel were added 1.998 g of the product prepared in Example 1 and 100 cc of purified water. The mixture was stirred until a clear solution resulted. Thereafter, 100 g of a 1% barium chloride solution were slowly added, with stirring, resulting in the formation of a precipitate (i.e., barium sulfate). The reaction mixture was filtered and the precipitate was washed with purified water several times and thereafter dried at 85° C. in a vacuum oven. The weight of the dried precipitate was 0.6721 g. The theoretical amount of barium sulfate was 0.6758 g. Accordingly, the purity of the stabilized glucosamine sulfate was 99%.

What is claimed is:

1. Glucosamine sulfate having a purity level of at least 99 wt. % and a maximum halide content of about 0.01 wt. %.

2. The glucosamine sulfate of claim 1 further comprising a pharmaceutically acceptable polymer.

3. The glucosamine sulfate of claim 2 wherein the polymer is present in an amount of about 2 to about 70 parts by weight per part of the glucosamine sulfate.

4. The glucosamine sulfate of claim 2 wherein the polymer comprises a water-soluble, water-dispersible and/or a water-swellable homopolymer and/or copolymer.

5. The glucosamine sulfate of claim 2 wherein the polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

6. A composition comprising glucosamine sulfate coated with a pharmaceutically acceptable polymer such that the coated glucosamine sulfate will be stable upon exposure to the atmosphere and/or ambient temperature, said glucosamine sulfate having a purity level of at least about 99 wt. % and a maximum halide content of about 0.01 wt. %.

7. The composition of claim 6 wherein the pharmaceutically acceptable polymer comprises a water-soluble, water-dispersible and/or a water-swellable homopolymer and/or copolymer.

8. The composition of claim 6 wherein the pharmaceutically acceptable polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

9. The composition of claim 6 wherein the pharmaceutically acceptable polymer is present in the composition in an amount of about 2 to about 70 parts by weight, per part of the glucosamine sulfate present in the composition.

10. A method for preparing glucosamine sulfate that comprises the steps of:
   (a) dissolving glucosamine base in water, said glucosamine base having a purity level of at least about 99.0 wt. % and a maximum halide content of about 0.01 wt. %;
   (b) adding a stoichiometric amount of aqueous sulfuric acid to the aqueous solution resulting from step (a); and
   (c) recovering glucosamine sulfate from the reaction mixture produced in step (b).

11. The method of claim 10 further comprising adding a pharmaceutically acceptable polymer to the reaction mixture resulting from step (a) prior to carrying out step (b) such that a stabilized glucosamine sulfate composition is recovered in step (c).

12. The method of claim 11 wherein the pharmaceutically acceptable polymer comprises a water-soluble, water-dispersible and/or a water-swellable homopolymer and/or copolymer.

13. The method of claim 11 wherein the pharmaceutically acceptable polymer is selected from the group consisting of carboxypolymethylene homopolymers and copolymers; polyethylene glycol homopolymers and copolymers; polypropylene glycol homopolymers and copolymers; ethylcellulose; povidone homopolymers and copolymers; polyacrylic acid homopolymers and copolymers; polyacrylamide homopolymers and copolymers; polysaccharides; and mixtures of two or more of the foregoing polymers.

14. The method of claim 11 wherein the pharmaceutically acceptable polymer is added to the reaction mixture in an amount of about 2 to about 70 parts by weight, per part of the glucosamine sulfate.

15. The method of claim 10 herein step (c) is carried out by adding a water-miscible solvent to the reaction mixture so as to precipitate the glucosamine sulfate composition therefrom.

16. The method of claim 15 wherein the solvent comprises acetone.

17. The method of claim 10 wherein step (c) is carried out by freeze-drying.

18. The method of claim 17 wherein the freeze-drying is carried out at a pressure of not greater than about 500 milliTorre and at a temperature of about −60 to about −20° C.

* * * * *